United States Patent [19]

Kataoka et al.

[11] Patent Number: 6,051,234
[45] Date of Patent: Apr. 18, 2000

[54] HEALTH DIET FOR PREVENTING DISEASES CAUSED BY LIFE-HABIT

[75] Inventors: Shigehiro Kataoka; Akio Obata; Jun Yamakoshi, all of Noda; Yukihiko Iwai, Kasukabe; Tatuo Manaka, Iwai; Toru Izumi, Noda; Koichiro Tobe, Noda; Nobuyuki Yamaji, Noda, all of Japan

[73] Assignee: Kikkoman Corporation, Noda, Japan

[21] Appl. No.: 09/018,437

[22] Filed: Feb. 4, 1998

[30] Foreign Application Priority Data

Feb. 6, 1997 [JP] Japan .................................... 9-036905

[51] Int. Cl.⁷ ............................ A61K 35/78; A23L 1/31; A23L 1/28
[52] U.S. Cl. ......................... 424/195.1; 426/49; 426/615; 426/648; 426/426; 426/489; 530/418; 530/422; 530/427; 424/439; 424/451; 424/464
[58] Field of Search ................................. 424/195.1, 439, 424/451, 464; 530/418, 422, 427; 426/49, 615, 648, 426, 489

[56] References Cited

U.S. PATENT DOCUMENTS 3,699,158  10/1972  Putter ....................................... 562/445
4,696,914  9/1987   Russe et al. ............................... 514/19
5,726,034  3/1998   Bryan et al. .............................. 435/68.1

FOREIGN PATENT DOCUMENTS

| 0 101 639 | 2/1984 | European Pat. Off. . |
| 55-055663 | 7/1980 | Japan . |
| 57-052362 | 11/1982 | Japan . |
| 405170756 | 7/1993 | Japan . |
| 5-170756 | 7/1993 | Japan . |
| 50170756 | 7/1993 | Japan . |
| 07010821 | 1/1995 | Japan . |
| 09187 244 | 7/1997 | Japan . |
| WO 96 10341A | 4/1996 | WIPO . |

*Primary Examiner*—Leon B. Lankford, Jr.
*Assistant Examiner*—Christopher R. Tate
*Attorney, Agent, or Firm*—Banner & Witcoff, Ltd.

[57] ABSTRACT

A health diet for preventing life-habit diseases (adult diseases) is provided.

The health diet is prepared by directly encapsulating or tableting an organic solvent extract of soy sauce cakes or an aqueous alkali extract of a soy sauce oil, or blending the extracts with a diet.

4 Claims, 1 Drawing Sheet

\* SIGNIFICANT AT A SIGNIFICANT LEVEL OF 10%

\*\* SIGNIFICANT AT A SIGNIFICANT LEVEL OF 5%

HEALTH DIET FOR PREVENTING DISEASES CAUSED BY LIFE-HABIT

BACKGROUND OF THE INVENTION

1. Field of the Invention

The present invention relates to health diets for preventing or alleviating life-habit diseases (adult diseases) due to biased diet which has been recently discussed, specifically to a health diet for preventing life-habit diseases which comprises as an effective ingredient an organic solvent extract of soy sauce cakes or an alkaline water extract of a soy sauce oil.

2. Description of the Related Prior Art

There have recently been pointed out the insufficient ingestion of calcium, vegetables and celluloses while with the sufficient ingestion of high fat and high protein foods by the diversification of dietary habits. Such life-habits as unbalanced diet or lack of exercise involve in the crisis or progression of diseases such as arterial screlosis, hyperpiesia, diabetes as well as cancer, osteoporosis, menopausal syndrome, and it is realized again that dietary life is important for preventing these diseases.

It has also been reported that osteoporosis is a serious problem accompanied by aging and postmenopausal patients of fracture reached 1.5 millions every year in United States of America as well as in Japan (Cooper, C. et al., Amer. J. Epidem., 1001, 1993; Riggd, B. L., West. J. Med., 154, 63, 1991). The economic requirement for curing osteoporosis amounts to enormous level, so that it is an important problem to prevent osteoporosis.

There have been thus proposed the maintenance of health or the prophylaxis of diseases by using effective ingredients of foods or foodstuffs.

There have been proposed a health food containing the strained draff of moromi produced in the brewing of rice vinegar which exhibits the obesity inhibiting, fresh skin maintaining and lipid peroxide inhibiting effects (Japanese Patent Kokoku No. 3-32347), foods containing lactoferrin for preventing aging (Japanese Patent Kokai No. 4-58871), and a health food containing chitin and calcium (Japanese Patent Kokai No. 5-255094).

However, there has been still demanded a health diet which can prevent more effectively the life-habit diseases such as osteoporosis, cancer, menopausal syndrome or arterial screlosis.

SUMMARY OF THE INVENTION

While it has been intensively realized that soy bean, especially its ingredients such as isoflavonoids and saponins are effective against osteoporosis or cancer, we directed our attention to the soy sauce cakes or the soy sauce oil which have been used only for the feed of domestic animals and have not been investigated on their pharmacological properties or the prophylactic effects of life-habit diseases. As a result of research, we have found that the organic solvent extract of soy sauce dregs or the alkaline water extract of soy sauce oils are effective against diseases such as osteoporosis, menopausal syndrome or arterial screlosis.

That is to say, the present invention is a health diet comprising the organic solvent extract of soy sauce dregs or the alkaline water extract of soy sauce oils.

DETAILED DESCRIPTION OF THE INVENTION

Figure 1:
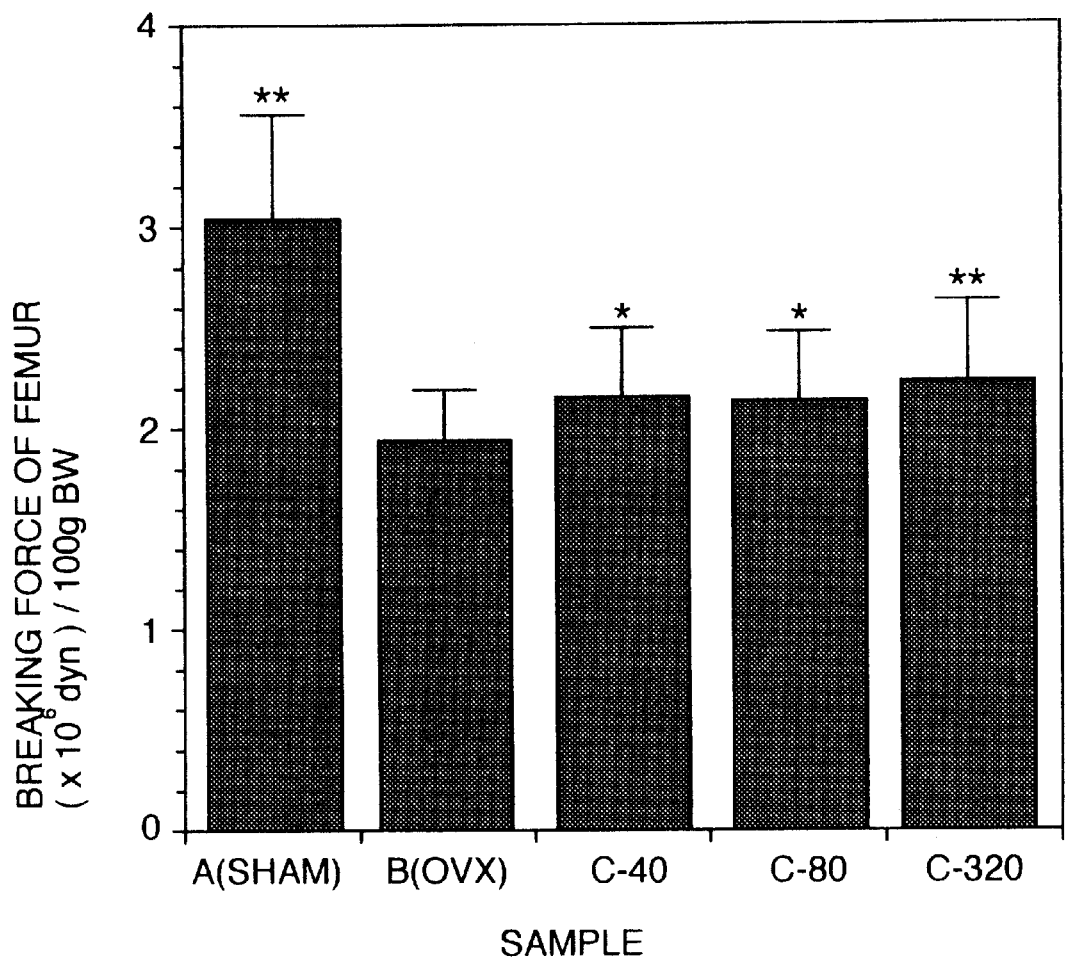
FIG. 1 represents the breaking force of the middle part of rat femur.

The present invention is now described specifically below.

The raw materials of the health diet of the present invention are the soy sauce cakes or the soy sauce oil which are produced during the process of producing soy sauce, and the effective ingredients comprises the organic solvent extract of soy sauce dregs or the alkaline water extract of soy sauce oils.

The soy sauce cakes or the soy sauce oil used as the raw materials are obtained as the by-products during the conventional production processes of soy sauce in both classic brewing and new brewing methods using whole soy bean, dehusked soy bean, defatted soy bean, or wheat as raw materials.

When the soy sauce cakes are used as the raw material, they are extracted with an organic solvent such as acetic acid, ethanol, methanol or ethyl acetate, preferably with a 50–100% aqueous alcohol in an amount of 2–20 times to the cakes, and the alcohol is removed by evaporation to give the extract.

Extraction is usually conducted at a temperature of 5° C. to the boiling point of the solvent used, preferably at 10–80° C.

In this connection, the lesser amount of the solvent is required if the first extract is used as an extracting solvent in the second stage, and the extraction efficiency is increased by using a continuous countercurrent extractor.

The extract thus obtained is directly concentrated to dryness, formed into powder, tablets, capsules as a health food, or added to a variety of beverages or foods to give a health diet for preventing the life-habit diseases.

In addition, such organic solvent extract contains a large amount of oils, which can be removed in the following procedure to give an extract.

After the organic solvent extract of the soy sauce cakes is concentrated, 1–8 M alkaline water is added to the concentrate thus obtained to adjust the pH to 9 or more, preferably 9–12, and the mixture is blended.

The alkaline water used is preferably aqueous ammonia, sodium hydroxide, potassium hydroxide, sodium carbonate, potassium carbonate, and the like. When the alkaline water is added and blended, the mixture is separated into an oil layer and an aqueous alkaline layer, and the alkaline aqueous layer is recovered. In this connection, the mixture can be heated or a saline, an alcohol, a commercially available separation promoting agent can be added in order to promote the separation.

An acidic solution is added to the alkaline aqueous layer separated to adjust the pH to 5 or less, preferably 3–5 to produce a precipitate.

The acid used is preferably the one which can be used as a food additive such as hydrochloric acid, acetic acid, phosphoric acid, succinic acid, and sulfuric acid.

The resulting precipitate is preferably decolored or deodorized by washing with water or treatment with active carbon, and the precipitate thus obtained is dehydrated by the conventional methods such as lyophilization or vacuum drying, formed into powder, tablets, capsules as a health food, or added to a variety of beverages or foods to give a health diet for preventing the life-habit diseases.

When the soy sauce oil is used as the raw material, 1–8 M aqueous alkaline is added to the soy sauce oil to adjust the pH to 9 or more, preferably 9–12, and the mixture is blended.

The alkaline water is preferably aqueous ammonia, sodium hydroxide, potassium hydroxide, sodium carbonate, potassium carbonate, and the like. When the alkaline water is added and blended, the mixture is separated into an oil layer and an aqueous alkaline layer, and the alkaline aqueous layer is recovered. In this connection, the mixture can be heated or a saline, an alcohol, a commercially available separation promoting agent can be added in order to promote the separation.

An acidic solution is added to the alkaline aqueous layer separated to adjust the pH to 5 or less, preferably 3–5 to produce a precipitate.

The acid used is preferably the one which is used as a food additive such as hydrochloric acid, acetic acid, phosphoric acid, succinic acid, and sulfuric acid.

The resulting precipitate is preferably decolored or deodorized by washing with water or treatment with active carbon, and the precipitate thus obtained is dehydrated by the conventional methods such as lyophilization or vacuum drying, formed into powder, tablets, capsules as a health food, or added to a variety of beverages or foods to give a health diet for preventing the life-habit diseases.

When the extract of the soy sauce cakes or soy sauce oil thus obtained is intended to use as a health food, it can be blended with a well-known excipient or the other additives so as to the ingested amount of the extract by an adult to be in a range of 0.001–10 g, preferably 0.01–4 g per day, and thus it can be formed into the conventional health foods such as powder, tablets, capsules, granules, syrup, or suspension.

Also, when the extract is added to a diet, it is sufficient to add the extract so as to be ingested by an adult in an amount of 0.001–10 g, preferably 0.01–4 g per day, for example in a proportion of 0.01–20%, preferably 0.05–10% of the diet.

The health diet for preventing life-habit diseases thus obtained is effective for the prophilaxis and alleviation of the life-habit diseases such as osteoporosis, menopausal syndrome or atherosclerosis.

Such effects are confirmed by the following test examples. In this connection, the soy sauce cakes and the soy sauce oil are the ones obtained during the production process of soy sauce from processed defatted soy bean as the raw material of protein by the classical brewing method.

TEST EXAMPLE 1

Confirmation Test of the Prophilactic Effect on Arterial Screlosis

Five groups of New Zealand white rabbits (male, 2–2.5 kg, 6 animals/group) comprising the normal diet administered group (group A) to which a powder feed for rabbits (RM-4, Funabashi Farm Co.) was administered, the control group (group B) to which the diet having added thereto 1% by weight of cholesterol was administered, the present invention test group (group C) to which the diet having added thereto 1% by weight of cholesterol followed by 3.8% by weight of the extract of the soy sauce cakes obtained in Example 2 was administered, the catechin administered group (group D) to which the diet having added thereto 1% by weight of cholesterol and blended with 1% by weight of catechin as a dietary ingredient which is known to have the anti-arterial screlotic effect is administered, and the probucol administered group (group E) as the positive control to which 1% by weight of cholesterol and 1% by weight of probucol as a pharmaceutical having an anti-arterial screlotic effect is administered were subjected to the test for comparison.

The above-described diet were administered in a limited amount of 90 g/rabbit/day every day for 2 months. During the test period, blood was sampled from otic artery to determine the lipid peroxides in serum. After the test was completed, the animals were dissected under anesthesia with nembutal, and aorta was delivered, immobilized with formalin, stained with Sudan IV to determine the ratio of the area of atherosclerotic lesion to the total area of aortic lumen with an image analyzer (SP 500F, Olympus Co.). Table 1 shows the values of serum lipid peroxides on the sixth week and the eighth week. Table 2 shows the ratios of the atherosclerotic lesions in aorta.

As is apparent from the result of Table 1, the groups D and E do not decrease the lipid peroxide content in serum, while the group C as the present invention test group significantly lowered the content.

It is thus estimated that the extract of the soy sauce cakes controls the oxidation of LDL involved in the crisis of atherosclerosis.

It is also found from Table 2 that the present invention test group (group C) decreases significantly the atherosclerotic lesion in aortic arch, and its effect is more intense than those of the groups D or E. It is also found that the present invention test group tends to decrease the atherosclerotic lesion in pars thoracic aorta, and thus it is suggested that the ingestion of the extract of soy sauce cakes is effective for the prophilaxis and alleviation of atherosclerosis.

TABLE 1

Serum lipid peroxides

| Test group | Sixth week | Eighth week |
| --- | --- | --- |
| A | 2.60 ± 1.29 ($\mu$mol/ml) | 2.57 ± 0.73 ($\mu$mol/ml) |
| B | 5.74 ± 0.73 | 5.15 ± 0.92 |
| C | 4.45 ± 0.35 *** | 3.70 ± 0.40 *** |
| D | 5.33 ± 1.16 | 5.05 ± 0.55 |
| E | 5.31 ± 1.61 | 4.84 ± 1.32 |

*** significant at a significant level of 1%.

TABLE 2

Anti-atherosclerotic activity
Percentage of initial surface area covered by atherosclerotic lesions

| Test group | Aortic arch | Thoracic aorta |
| --- | --- | --- |
| A | 0 | 0 |
| B | 68.3 ± 4.3 | 14.9 ± 12.3 |
| C | 31.4 ± 11.8 *** | 3.1 ± 3.1 |
| D | 55.2 ± 7.7 ** | 9.5 ± 7.5 |
| E | 51.9 ± 7.3 *** | 7.1 ± 8.4 |

** significant at a significant level of 5%.
*** significant at a significant level of 1%.

TEST EXAMPLE 2

Test of the Prophilactic Effect on Menopausal Disorders

SD rats (6 weeks, 150 g weight, 6 animals/group) were ovariectomized to make them menopausal. From the next day on, the present invention groups (groups A-10 and A-20) to which the normal diet (MF powder feed, ORIENTAL YEAST CO.) having added thereto the extract of the soy sauce oil obtained by the method described in Example 3 was administered in an amount of 10 mg/rat and 20 mg/rat, respectively, at the limited amount of 15 g/day, and the control group (group B) to which only the normal diet was administered in the same condition as above were subjected to the measurement of the temperature of the tail skin of each animal every week.

In this connection, it has been already described that when a rat is ovariectomized to make it menopausal, temperature rises from the early stage resulting in the hot flash when woman is in menopause (T. Kobayashi et al., J. Endocrinology, 146, 431, 1995).

The result of the test is shown in Table 3. The numerical values are the averages of the data obtained from six animals.

TABLE 3

| Test group | Skin temperature Week(s) in which skin temperature (° C.) was determined | | | | | | | |
| --- | --- | --- | --- | --- | --- | --- | --- | --- |
| | 0 | 1 | 2 | 3 | 4 | 5 | 6 | 7 |
| A-10 | 27.0 | 26.0 | 28.0 | 28.5 | 30.0 | 30.9 | 29.6 | 28.0 |
| A-20 | 27.0 | 26.0 | 28.0 | 28.5 | 29.6 | 30.2 | 29.1 | 28.0 |
| B | 27.0 | 27.5 | 28.7 | 28.9 | 30.5 | 30.9 | 29.2 | 28.2 |

As shown in Table 3, the skin temperature started to rise from the two or three weeks after ovariectomy and was maintained until about six weeks. In the animal groups (A-10, A-20) to which the extract of soy sauce oil was administered, the rise of the skin temperature was controlled more effectively than in the group B. These result indicates that the ingestion of the extract of the soy sauce oil is effective for the prevention or alleviation of menopausal disorders such as hot flash.

TEST EXAMPLE 3

Confirmation Test of the Effect on Osteoporosis

Eight SD rats (6 weeks, 150 g weight) per group were used for the test. The low Ca diet (0.01% Ca, 0.3% P) was administered to the group which was subjected to simulated surgery without ovariectomy (SHAM: group A) and the control group which was ovariectomized (OVX: group B), while the low Ca diet to which the extract of the soy sauce cakes was added in an amount of 40 mg/kg BW, 80 mg/kg BW and 320 mg/kg BW, respectively, were administered to the ovariectomized rats (group C) from the day after ovariectomy. The diet were given to all groups at the limited amount of 15 g/day.

After six weeks from the initiation of administration, femur was taken out and broken at the middle of the bone with a fracture property analyzer (DYN-1255, IIO DENKI) to measure the breaking force.

The results are illustrated in FIG. 1.

As is apparent from FIG. 1, the breaking force was lowered in the group B (OVX) which had been ovariectomized as compared with the group A (SHAM) which had been sham-operated. In all of the groups C to which the extract of the soy sauce cakes had been administered, the breaking force was increased significantly as compared with that in the group B. These results indicates that the extract of the soy sauce cakes prevents the decrease of bone salts on the induction of osteoporosis at postmenopausal stage and thus is effective for the prevention or alleviation of osteoporosis at postmenopausal stage.

EXAMPLES

The present invention is now described with reference to examples, which should not be construed as the limitation of the invention.

Example 1

Preparation of the Extract of Soy Sauce Cakes—1

Five hundred grams of say sauce cakes were extracted with 80% ethanol (2 l), passed through a filter, and concentrated to dryness under reduced pressure. The dry concentrate thus obtained was defatted with hexane (150 ml), and the residue was washed with aqueous ethanol and dried to give an extract of the soy sauce cakes in the form of powder (5 g).

Example 2

Preparation of the Extract of Soy Sauce Cakes—2

Soy sauce cakes (20 kg) were extracted with 90% ethanol (40 liter) in circulation, and the extract obtained was concentrated under reduced pressure to give a concentrate (6 liter).

To the concentrate was added 4 M sodium hydroxide solution (ca. 1 liter) to adjust the pH to 10, and the mixture was left standing overnight to separate the oil layer and the alkaline aqueous layer. The alkaline aqueous layer was adjusted to pH 4 with concentrated hydrochloric acid to produce a precipitate, which was collected by filtration, washed and lyophilized to give 100 g of an extract of the soy sauce cakes in the form of powder.

Example 3

Preparation of the Extract of Soy Sauce Oil

A sodium hydroxide solution was added to 2 kg of a soy sauce oil obtained in the production process of soy sauce to give 8 l of a mixed solution having a pH of 10. The mixture was left standing overnight to separate the oil layer and the alkaline aqueous layer. The alkaline aqueous layer thus obtained was adjusted to pH 4 with concentrated hydrochloric acid to produce a precipitate, which was adjusted to pH of 10 with 4 M sodium hydroxide solution, and then acidified again to pH 4 with concentrated hydrochloric acid to give a precipitate. The precipitate was collected by filtration, washed and lyophilized to give 2.0 g of an extract of the soy sauce oil in the form of powder.

The extract obtained as above, for example the one obtained in Example 2 had the composition of 0.7% of fibers, 13.9% of proteins, 10.3% of ashes, 2.6% of lipids, 5.0% of water, and 67.5% of carbohydrates. (In this case, the value of carbohydrates was the balance of 100 subtracting the contents of all the other ingredients.)

Example 4

Preparation of a Health Food in the Form of a Hard Capsule

| | |
| --- | --- |
| Extract of soy sauce cakes | 300 g |
| Potato starch | 150 g |
| Light silicic anhydride | 50 g |
| Calcium stearate | 10 g |
| Lactose | 490 g |

Above ingredients were blended homogeneously, and charged into hard capsules in an amount of 250 mg to give a health food.

The extract of the soy sauce cakes used is the one which was prepared in the method described in Example 2.

Example 5

Preparation of a Health Food in the Form of a Tablet

| | |
|---|---|
| Extract of soy sauce oil | 50 g |
| Lactose | 545 g |
| Potato starch | 250 g |
| Crystalline cellulose | 60 g |
| Light silicic anhydride | 50 g |
| Hydroxypropyl cellulose | 30 g |
| Magnesium stearate | 15 g |

After blending the extract of the soy sauce oil, lactose, potato starch, crystalline cellulose and light silicic anhydride, a 10% ethanol solution of hydroxypropyl cellulose was added, and the mixture was granulated by kneading and extruded through a screen having a diameter of 0.8 mm to give a granule, which was dried, blended with magnesium stearate, and subjected to compression molding to give a tablet having a weight of 250 mg/tablet.

The extract of the soy sauce oil used is the one which was prepared in the same manner as in Example 3.

Example 6

Health Food of a Tablet Type

| | |
|---|---|
| Extract of soy sauce cakes | 100 g |
| Calcium carbonate | 700 g |
| Lactose | 100 g |
| Crystalline cellulose | 55 g |
| Hydroxypropyl cellulose | 30 g |
| Calcium stearate | 10 g |
| Vitamin $D_3$ (50,000 IU/g) | 5 g |

After blending the extract of the soy sauce cakes, calcium carbonate, lactose, crystalline cellulose and vitamin D, a 10% ethanol solution of hydroxypropyl cellulose was added, and the mixture was granulated by kneading and extruded through a screen having a diameter of 0.8 mm to give a granule, which was dried, blended with calcium stearate, and subjected to compression molding to give a tablet having a weight of 500 mg.

The extract of the soy sauce cakes used is the one which was prepared in the same manner as in Example 2.

Preparation examples of health food containing the product according to the present invention are shown in the following.

Example 7

A potage soup having the following formulation was prepared by the conventional method.

In this case, the extract of the soy sauce cakes used is the one which was prepared in the same manner as in Example 2.

| | |
|---|---|
| Dry wheat | 389.5 g |
| Skimmed milk powder | 245 g |
| Refined tallow | 100 g |
| Starch | 50 g |
| Onion powder | 50 g |
| AMIFLEX A1 | 30 g |
| Anhydrous glucose | 30 g |
| Sucrose | 30 g |
| Chicken bouillon | 30 g |
| Salt | 20 g |
| Butter | 20 g |
| White pepper | 1.5 g |
| Extract of soy sauce cakes | 2.5 g |
| Vitamin E | 1 g |
| Turmeric | 0.5 g |

Example 8

A candy having the following formulation was prepared.

The extract of the soy sauce oil used is the one which was prepared in the same manner as in Example 3.

| | |
|---|---|
| Sucrose | 470 g |
| Corn syrup | 420 g |
| Water | 50 g |
| Fruit juice | 26 g |
| Thickening agent | 20 g |
| Ascorbic acid | 10.5 g |
| Extract of soy sauce oil | 2 g |
| Aroma | 1 g |
| β-Carotene | 0.5 g |

Example 9

A caramel having the following formulation was prepared.

In this case, the extract of the soy sauce cakes used is the one which was prepared in the same manner as in Example 2.

| | |
|---|---|
| Sucrose | 350 g |
| Corn syrup | 350 g |
| Condensed milk | 250 g |
| Butter | 40 g |
| Salt | 6 g |
| Extract of soy sauce cakes | 2 g |
| Perfume | 1 g |
| Vitamin E | 1 g |

Example 10

A chocolate having the following formulation was prepared.

In this case, the extract of the soy sauce cakes used is the one which was prepared in the same manner as in Example 2.

| | |
|---|---|
| Cocoa mass | 484.5 g |
| Cocoa butter | 130 g |
| Sucrose | 190 g |
| Whole milk powder | 190 g |
| Extract of soy sauce cakes | 3 g |
| Lecithin | 2 g |
| Aroma | 0.5 g |

What is claimed is:

1. A process for preparing a health-supplementing food product, the process comprising the following steps:

(1) extracting soy sauce cakes with an alcohol solvent;
(2) removing the alcohol solvent from the extract to obtain a concentrate;
(3) adding an aqueous alkali solution to the concentrate to ensure that the alkaline-treated concentrate has a pH of 9 or more and separating the alkaline-treated concentrate into an oil layer and an aqueous alkaline layer;
(4) recovering the aqueous alkaline layer and adjusting the pH of said aqueous alkaline layer to 5 or less to form a precipitate; and
(5) molding the precipitate into a powder, a tablet, or a capsule as said health-supplementing food product.

2. A method for treating menopausal syndrome, the method comprising administering to a subject having menopausal syndrome a therapeutically effective amount of the health-supplementing food product prepared by the process of claim 1.

3. A process for preparing a health-supplementing food product, the process comprising the following steps:
(1) adding an aqueous alkali solution to a soy sauce oil to ensure that the alkaline-treated oil has a pH of 9 or more, and separating the alkaline-treated oil into an oil layer and an aqueous alkaline layer;
(2) recovering the aqueous alkaline layer and adjusting the pH of the aqueous alkaline layer to 5 or less to form a precipitate; and
(3) molding the precipitate into a powder, a tablet, or a capsule as said health-supplementing food product.

4. A method for treating menopausal syndrome, the method comprising administering to a subject having menopausal syndrome a therapeutically effective amount of the health-supplementing food product prepared by the process of claim 3.

* * * * *